United States Patent
Liu et al.

(10) Patent No.: US 11,634,522 B2
(45) Date of Patent: Apr. 25, 2023

(54) STYRENE DERIVATIVE AND PREPARATION METHOD THEREOF, AND MODIFIED ORGANIC SILICONE RESIN AND PREPARATION METHOD AND USE THEREOF

(71) Applicants: ZHUOLI IMAGING TECHNOLOGY CO., LTD., Henan (CN); INSTITUTE OF CHEMISTRY CO. LTD HENAN ACADEMY OF SCIENCES, Henan (CN)

(72) Inventors: Pengju Liu, Henan (CN); Xiufeng Yue, Henan (CN); Shengqiao He, Henan (CN); Lixia Deng, Henan (CN); Fei Yang, Henan (CN); Libing Guo, Henan (CN)

(73) Assignees: ZHUOLI IMAGING TECHNOLOGY CO., LTD, Jiaozuo (CN); INSTITUTE OF CHEMISTRY CO. LTD HENAN ACADEMY OF SCIENCES, Zhengzhou (CN)

( * ) Notice: Subject to any disclaimer, the term of this patent is extended or adjusted under 35 U.S.C. 154(b) by 0 days.

(21) Appl. No.: 17/843,017

(22) Filed: Jun. 17, 2022

(65) Prior Publication Data
US 2023/0025924 A1 Jan. 26, 2023

Related U.S. Application Data

(63) Continuation of application No. PCT/CN2022/070224, filed on Jan. 5, 2022.

(30) Foreign Application Priority Data

Jun. 24, 2021 (CN) .......................... 202110704551.6

(51) Int. Cl.
C08F 212/14 (2006.01)
C07C 25/28 (2006.01)
(Continued)

(52) U.S. Cl.
CPC .......... C08F 212/08 (2013.01); C08F 212/20 (2020.02); C08F 220/06 (2013.01);
(Continued)

(58) Field of Classification Search
None
See application file for complete search history.

(56) References Cited

U.S. PATENT DOCUMENTS 5,182,252 A 1/1993 Nagasawa et al.

FOREIGN PATENT DOCUMENTS

CN 107353189 A 11/2017
CN 107779202 A * 3/2018 ......... C09K 19/3028
(Continued)

OTHER PUBLICATIONS

Ivaylo Dimitrov, "Controlled Synthesis of Fluorinated Copolymers with Pendant Sulfonates", Journal of Polymer Science: Part A: Polymer Chemistry, vol. 46, 7827-7834, 2008 Wiley Periodicals, Inc., pp. 7827-7834.
(Continued)

Primary Examiner — Richard A Huhn
(74) Attorney, Agent, or Firm — Brundidge & Stanger, P.C.

(57) ABSTRACT

The present disclosure provides a styrene derivative and a preparation method thereof, and a modified organic silicone resin and a preparation method and use thereof, and belongs to the technical field of back coating solutions. The styrene derivative is specifically 2,3-difluoro-4-methoxystyrene. A fluorine atom is introduced into a benzene ring structure, and the obtained styrene derivative contains a C—F bond with a
(Continued)

relatively high chemical bond energy, such that the styrene derivative has a relatively high thermal stability. The styrene derivative can be introduced into an organic silicone resin to make the obtained modified organic silicone resin have a higher thermal stability. The modified organic silicone resin can be used as a back coating solution to effectively improve a heat resistance of barcode thermal transfer ribbons.

19 Claims, 1 Drawing Sheet

(51) Int. Cl.
*C07C 43/205* (2006.01)
*C07C 43/215* (2006.01)
*C07C 43/225* (2006.01)
*C08F 212/08* (2006.01)
*C08F 220/06* (2006.01)
*C08G 77/20* (2006.01)
*C08F 220/14* (2006.01)
*G09F 3/02* (2006.01)
*C09D 183/04* (2006.01)

(52) U.S. Cl.
CPC ............ *C08F 220/14* (2013.01); *C08G 77/20* (2013.01); *C07C 25/28* (2013.01); *C07C 43/205* (2013.01); *C07C 43/215* (2013.01); *C07C 43/225* (2013.01); *C08F 212/22* (2020.02); *C09D 183/04* (2013.01); *G09F 3/02* (2013.01)

(56) References Cited

FOREIGN PATENT DOCUMENTS

| | | |
|---|---|---|
| CN | 107779202 A | 3/2018 |
| CN | 111253524 A | 6/2020 |
| CN | 113429270 A | 9/2021 |

OTHER PUBLICATIONS

International Search Report of PCT/CN2022/070224.

\* cited by examiner

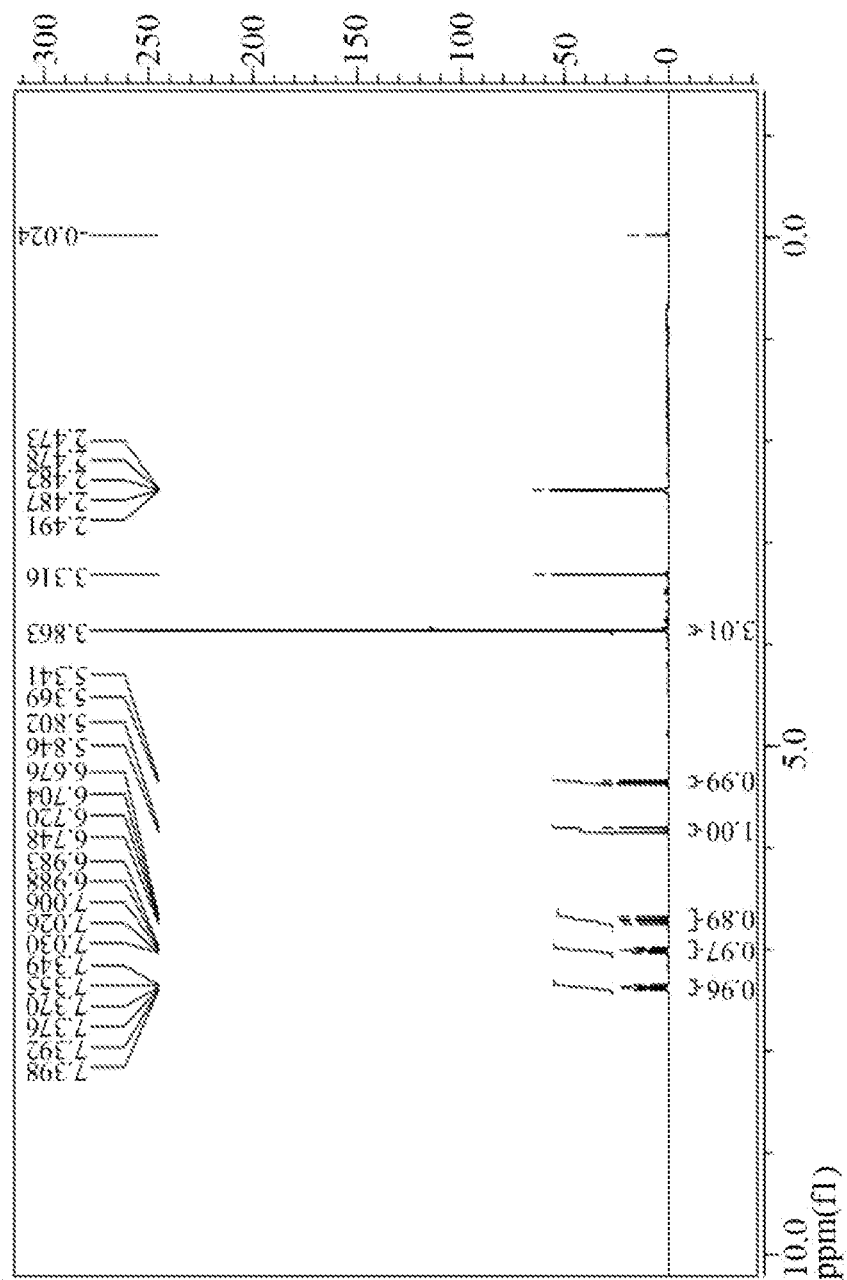

STYRENE DERIVATIVE AND PREPARATION METHOD THEREOF, AND MODIFIED ORGANIC SILICONE RESIN AND PREPARATION METHOD AND USE THEREOF

TECHNICAL FIELD

The present disclosure relates to the technical field of back coating solutions, in particular to a styrene derivative and a preparation method thereof, and a modified organic silicone resin and a preparation method and use thereof.

BACKGROUND ART

A back coating solution for barcode thermal transfer ribbons is a special substance coated on a back of the thermal transfer ribbons. After curing, the back coating solution forms a back coating for protection of a printing probe and tape bases such as a polyethylene terephthalate (PET)-based tape base. During printing, the printing probe applies pressure and heat to an ink-free side of the thermal transfer ribbons, to transfer corresponding barcode image information to a label. On a back of an ink side under pressure, the back coating plays a protective role to effectively increase a temperature resistance and smoothness of ink ribbons or ribbon base film.

Organic silicone resin-based back coating solution is one of the commonly used back coating solutions for barcode thermal transfer ribbons. Existing organic silicone resin-based back coating solutions are generally prepared based on styrene as a polymerizable monomer. With the improvement of printing rate and quality requirements, it is a technical problem to be solved urgently at present to further improve a heat resistance of the organic silicone resin-based back coating solutions.

SUMMARY

An objective of the present disclosure is to provide a styrene derivative and a preparation method thereof, and a modified organic silicone resin and a preparation method and use thereof. In the present disclosure, a fluorine atom is introduced into a benzene ring structure, and the obtained styrene derivative has a relatively high thermal stability. The styrene derivative can be introduced into an organic silicone resin to obtain a modified organic silicone resin. The modified organic silicone resin can be used as a back coating solution to effectively improve a heat resistance of barcode thermal transfer ribbons.

To achieve the above objective, the present disclosure provides the following technical solutions.

The present disclosure provides a styrene derivative, having a structure shown in formula I:

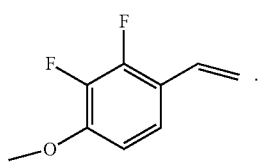

Formula I

The present disclosure further provides a preparation method of the styrene derivative, including the following steps:

mixing a methyltriphenylphosphonium bromide solution with a n-butyllithium (n-BuLi) solution in a protective atmosphere to obtain a phosphorus ylide reagent; and mixing the phosphorus ylide reagent with a 2,3-difluoro-4-methoxybenzaldehyde solution in a protective atmosphere to conduct a nucleophilic reaction, to obtain the styrene derivative having a structure shown in formula I.

Preferably, a mass of methyltriphenylphosphonium bromide in the methyltriphenylphosphonium bromide solution and a molar weight of n-BuLi in the n-BuLi solution may have a ratio of (1-3) kg:(6-10) mol.

Preferably, the methyltriphenylphosphonium bromide solution may have a concentration of 0.3 kg/L to 0.9 kg/L.

Preferably, the n-BuLi solution may have a concentration of 2 mol/L to 3 mol/L.

Preferably, a method for mixing the methyltriphenylphosphonium bromide solution with the n-BuLi solution may include the following step:

adding the n-BuLi solution dropwise to the methyltriphenylphosphonium bromide solution under an protective atmosphere at −100° C. to 0° C.

Preferably, a method for mixing the phosphorus ylide reagent with the 2,3-difluoro-4-methoxybenzaldehyde solution may include the following step:

adding the 2,3-difluoro-4-methoxybenzaldehyde solution dropwise to the phosphorus ylide reagent under an protective atmosphere at −10° C. to 10° C.

Preferably, the methyltriphenylphosphonium bromide solution and the 2,3-difluoro-4-methoxybenzaldehyde solution each may adopt an ethers-based organic solvent.

Preferably, the ethers-based organic solvent may include one or more selected from the group consisting of tetrahydrofuran, methyltetrahydrofuran, diethyl ether, and methyl tert-butyl ether.

Preferably, the n-BuLi solution may adopt n-hexane as a solvent.

Preferably, methyltriphenylphosphonium bromide in the methyltriphenylphosphonium bromide solution and 2,3-difluoro-4-methoxybenzaldehyde in the 2,3-difluoro-4-methoxybenzaldehyde solution may have a mass ratio of (1-3):1.

Preferably, the 2,3-difluoro-4-methoxybenzaldehyde solution may have a concentration of 0.3 kg/L to 1.5 kg/L.

Preferably, the nucleophilic reaction may be conducted at 15° C. to 35° C. for 6 h to 12 h.

The present disclosure further provides a modified organic silicone resin, prepared by the following raw materials: an acrylic acid derivative, a styrene derivative, methacryloxypropyl terminated polydimethylsiloxane, a free radical initiator, and an organic solvent, where the acrylic acid derivative, the styrene derivative, the methacryloxypropyl terminated polydimethylsiloxane, the free radical initiator, and the organic solvent have a mass ratio of (65-89):(1-5):(10-30):(0.1-2):(100-450); and the styrene derivative is the above-mentioned styrene derivative.

Preferably, the acrylic acid derivative may be one or more selected from the group consisting of methacrylic acid, acrylic acid, methacrylate, and acrylate.

Preferably, the methacryloxypropyl terminated polydimethylsiloxane may have a weight-average molecular weight of 10,000 to 40,000.

Preferably, the free radical initiator may include azobisisobutyronitrile and/or dibenzoyl peroxide.

Preferably, the organic solvent may include toluene and/or butanone.

The present disclosure further provides a preparation method of the modified organic silicone resin, including the following steps:

mixing the acrylic acid derivative, the styrene derivative, the methacryloxypropyl terminated polydimethylsiloxane, the free radical initiator, and the organic solvent to conduct polymerization, to obtain the modified organic silicone resin.

Preferably, the polymerization may be conducted at 80° C. to 120° C. for greater than or equal to 1.5 h.

The present disclosure further provides use of the modified organic silicone resin or a modified organic silicone resin prepared by the preparation method as a back coating solution for barcode thermal transfer ribbons.

The styrene derivative is specifically 2,3-difluoro-4-methoxystyrene. A fluorine atom is introduced into a benzene ring structure, and the obtained styrene derivative contains a C—F bond with a relatively high chemical bond energy, such that the styrene derivative has a relatively high thermal stability. The styrene derivative can be introduced into an organic silicone resin to make the obtained modified organic silicone resin have a higher thermal stability. The modified organic silicone resin can be used as a back coating solution to effectively improve a heat resistance of barcode thermal transfer ribbons.

In addition, the styrene derivative is introduced into the organic silicone resin to effectively improve a smoothness of the obtained modified organic silicone resin; the modified organic silicone resin is used as a back coating solution for barcode thermal transfer ribbons to effectively reduce a printing noise. Meanwhile, the styrene derivative has a lower surface energy due to introduction of the fluorine atom; the styrene derivative is introduced into the organic silicone resin to effectively improve an adhesive force and bonding capacity of the obtained modified organic silicone resin.

The preparation method of the styrene derivative has a low price and wide source of preparation raw materials. Skillfully, the phosphorus ylide reagent is used to prepare the styrene derivative, with simple operations, mild reaction conditions, high selectivity, few by-products, and excellent product yield and purity. Therefore, the preparation method is suitable for industrial production.

BRIEF DESCRIPTION OF THE DRAWINGS

FIG. 1 shows a hydrogen-nuclear magnetic resonance (H-NMR) spectrum of 2,3-difluoro-4-methoxystyrene prepared in Example 1.

DETAILED DESCRIPTION OF THE EMBODIMENTS

The present disclosure provides a styrene derivative, having a structure shown in formula I:

Formula I

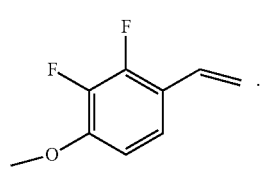

The styrene derivative has a chemical name of 2,3-difluoro-4-methoxystyrene.

The present disclosure further provides a preparation method of the styrene derivative, including the following steps:

mixing a methyltriphenylphosphonium bromide solution with a n-butyllithium (n-BuLi) solution in a protective atmosphere to obtain a phosphorus ylide reagent; and mixing the phosphorus ylide reagent with a 2,3-difluoro-4-methoxybenzaldehyde solution in a protective atmosphere to conduct a nucleophilic reaction, to obtain the styrene derivative having a structure shown in formula I.

In the present disclosure, unless otherwise specified, the raw materials used are all commercially-available commodities well known to those skilled in the art or prepared by methods well known to those skilled in the art.

In the present disclosure, there is no special limitation on a type of protective gas that provides the protective atmosphere during the preparation of the styrene derivative, and a protective gas well-known to those skilled in the art can be used, such as nitrogen.

In the present disclosure, the methyltriphenylphosphonium bromide solution is mixed with the n-BuLi solution in the protective atmosphere to obtain the phosphorus ylide reagent. A mass of methyltriphenylphosphonium bromide in the methyltriphenylphosphonium bromide solution and a molar weight of n-BuLi in the n-BuLi solution have a ratio of preferably (1-3) kg:(6-10) mol, more preferably (2-2.5) kg:(7.5-9) mol. A solvent in the methyltriphenylphosphonium bromide solution is preferably an ethers-based organic solvent, and the ethers-based organic solvent includes preferably one or more selected from the group consisting of tetrahydrofuran, methyltetrahydrofuran, diethyl ether, and methyl tert-butyl ether, more preferably the tetrahydrofuran; the ethers-based organic solvent is beneficial for stabilizing the phosphorus ylide reagent by forming adducts. The methyltriphenylphosphonium bromide solution has a concentration of preferably 0.3 kg/L to 0.9 kg/L, more preferably 0.5 kg/L to 0.7 kg/L. A solvent in the n-BuLi solution is preferably n-hexane; and the n-BuLi solution has a concentration of preferably 2 mol/L to 3 mol/L, more preferably 2.5 mol/L.

In the present disclosure, the n-BuLi solution is added preferably dropwise to the methyltriphenylphosphonium bromide solution under an protective atmosphere at −100° C. to 0° C. The methyltriphenylphosphonium bromide solution is mixed with the n-BuLi solution using liquid nitrogen to provide a low temperature at preferably −90° C. to −30° C., more preferably −80° C. to −50° C. The low temperature is beneficial to obtain a stable phosphorus ylide reagent. There is no special limitation on an adding rate dropwise of the n-BuLi solution, as long as a stable phosphorus ylide reagent can be obtained.

In the present disclosure, the phosphorus ylide reagent is mixed with the 2,3-difluoro-4-methoxybenzaldehyde solution in the protective atmosphere to conduct the nucleophilic reaction, to obtain the styrene derivative having a structure shown in formula I. Methyltriphenylphosphonium bromide in the methyltriphenylphosphonium bromide solution and 2,3-difluoro-4-methoxybenzaldehyde in the 2,3-difluoro-4-methoxybenzaldehyde solution have a mass ratio of preferably (1-3):1, more preferably (2-2.5):1. A solvent in the 2,3-difluoro-4-methoxybenzaldehyde solution is preferably an ethers-based organic solvent, and the ethers-based organic solvent includes preferably one or more selected from the group consisting of tetrahydrofuran, methyltetrahydrofuran, diethyl ether, and methyl tert-butyl ether, more preferably the tetrahydrofuran. The 2,3-difluoro-4-methoxybenzaldehyde solution has a concentration of preferably 0.3 kg/L to 1.5 kg/L, more preferably 0.5 kg/L to 1 kg/L.

In the present disclosure, the 2,3-difluoro-4-methoxybenzaldehyde solution is added preferably dropwise to the phosphorus ylide reagent under an protective atmosphere at −10° C. to 10° C. After the methyltriphenylphosphonium bromide solution is mixed with the n-BuLi solution, when the obtained phosphorus ylide reagent is lower than −10° C. to 10° C., the phosphorus ylide reagent is preferably naturally heated to a required temperature. The phosphorus ylide reagent is mixed with the 2,3-difluoro-4-methoxybenzaldehyde solution at more preferably 0° C. There is no special limitation on an adding rate dropwise of the 2,3-difluoro-4-methoxybenzaldehyde solution, and adding rates dropwise well known to those skilled in the art can be used.

In the present disclosure, the nucleophilic reaction is conducted at preferably 15° C. to 35° C., more preferably 20° C. to 30° C., and specifically at room temperature; in an example, the room temperature is specifically 25° C. The nucleophilic reaction is conducted for preferably 6 h to 12 h, more preferably 8 h to 12 h. The nucleophilic reaction is conducted by stirring; and there is no special limitation on a stirring rate, as long as the nucleophilic reaction is conducted smoothly. A reaction formula involved in the nucleophilic reaction is shown below:

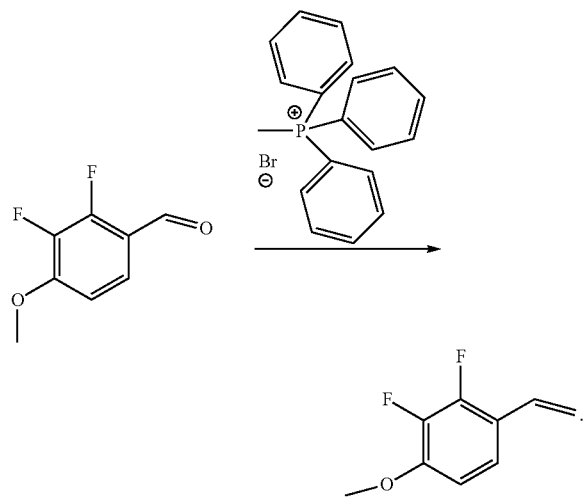

In the present disclosure, after the nucleophilic reaction, the method further includes preferably the following steps: adding water to an obtained system for quenching, and adding an extractant for extraction; washing an organic phase obtained from the extraction with water, and drying a washed organic phase with anhydrous sodium sulfate, filtering, and collecting a filtrate for rotary evaporation to remove the solvent; subjecting an obtained residue to vacuum distillation and rectification successively to obtain colorless liquid, namely the styrene derivative having a structure shown in formula I. The extractant is preferably selected from the group consisting of ethyl acetate, methyl acetate, diethyl ether, and butyl ether, more preferably the diethyl ether. The vacuum distillation and the rectification each are conducted preferably under a vacuum degree of 6 mmHg to 10 mmHg.

The present disclosure further provides a modified organic silicone resin, prepared by the following raw materials: an acrylic acid derivative, a styrene derivative, methacryloxypropyl terminated polydimethylsiloxane, a free radical initiator, and an organic solvent, where the acrylic acid derivative, the styrene derivative, the methacryloxypropyl terminated polydimethylsiloxane, the free radical initiator, and the organic solvent have a mass ratio of (65-89):(1-5):(10-30):(0.1-2):(100-450), preferably (70-78):(2-3):(15-25):(0.3-1):(200-350).

In the present disclosure, the acrylic acid derivative is preferably one or more selected from the group consisting of methacrylic acid, acrylic acid, methacrylate and acrylate, more preferably the methacrylic acid and the methacrylate; when the acrylic acid derivative is the methacrylic acid and the methacrylate, the methacrylic acid and the methacrylate have a mass ratio of preferably 1:(1-5), more preferably 1:(2-4).

In the present disclosure, the styrene derivative is the above-mentioned styrene derivative. The organic silicone resin is modified by the styrene derivative, such that the obtained modified organic silicone resin has a higher thermal stability. The modified organic silicone resin is used as a back coating solution for barcode thermal transfer ribbons to effectively improve a heat resistance, smoothness, adhesive force and bonding capacity, and to effectively reduce a printing noise.

In the present disclosure, the methacryloxypropyl terminated polydimethylsiloxane has a weight-average molecular weight of preferably 10,000 to 40,000, more preferably 20,000 to 30,000. The methacryloxypropyl terminated polydimethylsiloxane with the above weight-average molecular weight is beneficial to ensure that the obtained modified organic silicone resin has a relatively high thermal stability. The modified organic silicone resin is used as a back coating solution for barcode thermal transfer ribbons to effectively improve a heat resistance, smoothness, adhesive force and bonding capacity, and to effectively reduce a printing noise.

In the present disclosure, the free radical initiator includes preferably azobisisobutyronitrile (AIBN) and/or dibenzoyl peroxide (BPO), more preferably the AIBN or the BPO.

In the present disclosure, the organic solvent includes preferably toluene and/or butanone, that is, the toluene, or the butanone, or a mixture of the toluene and the butanone can be used; when the organic solvent is the mixture of the toluene and the butanone, there is no special limitation on a mass ratio of the toluene and the butanone, and the mass ratio can be specifically (2-4):(3-5), preferably 3:4.

The present disclosure further provides a preparation method of the modified organic silicone resin, including the following steps:

mixing the acrylic acid derivative, the styrene derivative, the methacryloxypropyl terminated polydimethylsiloxane, the free radical initiator, and the organic solvent to conduct polymerization, to obtain the modified organic silicone resin.

In the present disclosure, there is no special limitation on a method for mixing the acrylic acid derivative, the styrene derivative, the methacryloxypropyl terminated polydimethylsiloxane, the free radical initiator, and the organic solvent, as long as each component can be mixed evenly. The polymerization is conducted preferably under reflux conditions. Specifically, the polymerization is conducted preferably at 80° C. to 120° C., more preferably 85° C. to 115° C., and further more preferably 90° C. to 110° C. The polymerization is conducted for preferably greater than or equal to 1.5 h, more preferably 3 h to 4 h. Preferably, the acrylic acid derivative, the styrene derivative, the methacryloxypropyl terminated polydimethylsiloxane, and the free radical initiator are mixed with the organic solvent to obtain a mixed material. A part of the mixed material is heated to a reflux state, the reflux state is held, remaining mixed material is added dropwise to the part of the mixed material, and the reflux state is held to conduct the polymerization. The part of the mixed material accounts for preferably 7% to 15%, more preferably 9% to 10% of a total mass of the mixed material. There is no special limitation on an adding rate dropwise of the remaining mixed material, as long as a temperature of the system is guaranteed to be within a required range; the polymerization is specifically started after the remaining mixed material is completely added dropwise.

The present disclosure further provides use of the modified organic silicone resin or a modified organic silicone resin prepared by the preparation method as a back coating solution for barcode thermal transfer ribbons. 2,3-difluoro-4-methoxystyrene is introduced into the modified organic silicone resin. The modified organic silicone resin is used as a back coating solution for barcode thermal transfer ribbons, which can make a back coating formed after curing have excellent smoothness and heat resistance. Therefore, when printing at high rate or when a printing task is large, the back coating can ensure that the tape base is stable under pressure and may not be broken down due to severe heating. Meanwhile, the back coating has a strong adhesion, can be firmly combined with the tape base, and does not fall off and peel off during winding and unwinding of thermal transfer ribbons as well as printing. In addition, the back coating has a better lubricity. There is no special limitation on a specific method for using the modified organic silicone resin as the back coating solution for barcode thermal transfer ribbons, and methods well known to those skilled in the art can be used.

The technical solutions in the present disclosure are clearly and completely described below in conjunction with examples of the present disclosure. It is clear that the described examples are merely a part, rather than all of the examples of the present disclosure. All other examples obtained by a person of ordinary skill in the art based on the examples of the present disclosure without creative efforts shall fall within the protection scope of the present disclosure.

The 2,3-difluoro-4-methoxybenzaldehyde used in the following examples of the present disclosure was prepared according to the following steps:

under nitrogen protection, dissolving 1.7 kg of 2,3-difluoroanisole in 3 L of dichloromethane; at 0° C., adding a phosphorus ylide reagent of 5.6 kg of titanium tetrachloride and 6 L of the dichloromethane dropwise to an obtained system, stirring for 30 min, and adding 1.5 kg of dichloromethoxy-methan at 0° C., and conducting a reaction by stirring at room temperature (25° C.) for 2 h; washing an obtained product system with water, conducting liquid separation to obtain an organic phase, drying the organic phase by anhydrous sodium sulfate and filtering, concentrating an obtained filtrate, and dispersing an obtained residue in petroleum ether to precipitate crystals; and filtering the crystals to obtain 1.1 kg of the 2,3-difluoro-4-methoxybenzaldehyde as off-white and needle-like crystals.

Example 1

Under nitrogen protection, 2 kg of methyltriphenylphosphonium bromide was dissolved in 3 L of tetrahydrofuran to obtain a methyltriphenylphosphonium bromide solution; the methyltriphenylphosphonium bromide solution was placed in a reactor, the reactor was cooled to −78° C. by liquid nitrogen, and 3 L of a n-BuLi solution with a concentration of 2.5 M (using n-hexane as a solvent) was added dropwise to the reactor, and the reactor was naturally heated to 0° C. to obtain a yellow clear liquid; a mixed solution of 1 kg of 2,3-difluoro-4-methoxybenzaldehyde and 1 L of tetrahydrofuran was added dropwise to the yellow clear liquid, and a reaction was conducted by stirring at room temperature for 12 h; pure water was added to an obtained system for quenching, and extraction was conducted by diethyl ether; an obtained organic phase obtained from the extraction was washed with water, and a washed organic phase was dried with anhydrous sodium sulfate, and filtered; a filtrate was collected for rotary evaporation to remove the solvent; under a vacuum degree of 6 mmHg, an obtained residue was subjected to vacuum distillation and rectification successively to obtain colorless liquid, namely 2,3-difluoro-4-methoxystyrene, with a yield of 800 g and a purity of 98.2%.

FIG. 1 shows an H-NMR spectrum of 2,3-difluoro-4-methoxystyrene prepared in Example 1. The specific data are as follows:

$^1$H NMR (DMSO-$d_6$ 400 MHZ) δ: 7.398-6.983 (m, 2H, Ar—H), 6.748-6.676 (m, H, Ar—C—H), 5.846-5.341 (m, 2H, C=C—H), 3.01 (s, 3H, —O—CH$_3$).

Example 2

Under nitrogen protection, 2 kg of methyltriphenylphosphonium bromide was dissolved in 4 L of tetrahydrofuran to obtain a methyltriphenylphosphonium bromide solution; the methyltriphenylphosphonium bromide solution was placed in a reactor, the reactor was cooled to −45° C. by liquid nitrogen, and 3 L of a n-BuLi solution with a concentration of 2.5 M (using n-hexane as a solvent) was added dropwise to the reactor, and the reactor was naturally heated to 0° C. to obtain a yellow clear liquid; a mixed solution of 1 kg of 2,3-difluoro-4-methoxybenzaldehyde and 2 L of tetrahydrofuran was added dropwise to the yellow clear liquid, and a reaction was conducted by stirring at room temperature for 12 h; pure water was added to an obtained system for quenching, and extraction was conducted by diethyl ether; an obtained organic phase obtained from the extraction was washed with water, and a washed organic phase was dried with anhydrous sodium sulfate, and filtered; a filtrate was collected for rotary evaporation to remove the solvent; under a vacuum degree of 10 mmHg, an obtained residue was subjected to vacuum distillation and rectification successively to obtain colorless liquid, namely 2,3-difluoro-4-methoxystyrene, with a yield of 810 g and a purity of 98.4%.

Example 3

Under nitrogen protection, 2 kg of methyltriphenylphosphonium bromide was dissolved in 3 L of tetrahydrofuran to obtain a methyltriphenylphosphonium bromide solution; the methyltriphenylphosphonium bromide solution was placed in a reactor, the reactor was cooled to −78° C. by liquid nitrogen, and 3.5 L of a n-BuLi solution with a concentration of 2.5 M (using n-hexane as a solvent) was added dropwise to the reactor, and the reactor was naturally heated to 0° C. to obtain a yellow clear liquid; a mixed solution of 1 kg of 2,3-difluoro-4-methoxybenzaldehyde and 1 L of tetrahydrofuran was added dropwise to the yellow clear liquid, and a reaction was conducted by stirring at room temperature for 12 h; pure water was added to an obtained system for quenching, and extraction was conducted by diethyl ether; an obtained organic phase obtained from the extraction was washed with water, and a washed organic phase was dried with anhydrous sodium sulfate, and filtered; a filtrate was collected for rotary evaporation to remove the solvent; under a vacuum degree of 8 mmHg, an obtained residue was subjected to vacuum distillation and rectification successively to obtain colorless liquid, namely 2,3-difluoro-4-methoxystyrene, with a yield of 780 g and a purity of 98.1%.

Example 4

Under nitrogen protection, 2.5 kg of methyltriphenylphosphonium bromide was dissolved in 4 L of tetrahydrofuran to obtain a methyltriphenylphosphonium bromide solution; the methyltriphenylphosphonium bromide solution was placed in a reactor, the reactor was cooled to −78° C. by liquid nitrogen, and 4 L of a n-BuLi solution with a concentration of 2.5 M (using n-hexane as a solvent) was added dropwise to the reactor, and the reactor was naturally heated to 0° C. to obtain a yellow clear liquid; a mixed solution of 1 kg of 2,3-difluoro-4-methoxybenzaldehyde and 1 L of tetrahydrofuran was added dropwise to the yellow clear liquid, and a reaction was conducted by stirring at room temperature for 12 h; pure water was added to an obtained system for quenching, and extraction was conducted by diethyl ether; an obtained organic phase obtained from the extraction was washed with water, and a washed organic phase was dried with anhydrous sodium sulfate, and filtered; a filtrate was collected for rotary evaporation to remove the solvent; under a vacuum degree of 7 mmHg, an obtained residue was subjected to vacuum distillation and rectification successively to obtain colorless liquid, namely 2,3-difluoro-4-methoxystyrene, with a yield of 830 g and a purity of 98.2%.

Use Example 1

50 g of methacrylic acid, 181 g of methyl methacrylate, 9 g of 2,3-difluoro-4-methoxystyrene, 60 g of methacryloxypropyl terminated polydimethylsiloxane with a weight-average molecular weight of 20,000, 700 g of toluene and 1 g of AIBN were mixed uniformly to obtain a mixed material; 100 g of the mixed material was placed in a reaction flask, and heated to a reflux state (115° C.); the reflux state was held, the remaining mixed material was added dropwise into the reaction flask, and a reaction was conducted under the reflux state for 4 h to obtain a modified organic silicone resin.

Use Example 2

70 g of methacrylic acid, 147 g of methyl methacrylate, 8 g of 2,3-difluoro-4-methoxystyrene, 75 g of methacryloxypropyl terminated polydimethylsiloxane with a weight-average molecular weight of 25,000, 700 g of butanone and 1 g of BPO were mixed uniformly to obtain a mixed material; 100 g of the mixed material was placed in a reaction flask, and heated to a reflux state (85° C.); the reflux state was held, the remaining mixed material was added dropwise into the reaction flask, and a reaction was conducted under the reflux state for 4 h to obtain a modified organic silicone resin.

Use Example 3

50 g of methacrylic acid, 181 g of methyl methacrylate, 9 g of 2,3-difluoro-4-methoxystyrene, 60 g of methacryloxypropyl terminated polydimethylsiloxane with a weight-average molecular weight of 30,000, 300 g of toluene, 400 g of butanone and 1 g of AIBN were mixed uniformly to obtain a mixed material; 100 g of the mixed material was placed in a reaction flask, and heated to a reflux state (90° C.); the reflux state was held, the remaining mixed material was added dropwise into the reaction flask, and a reaction was conducted under the reflux state for 4 h to obtain a modified organic silicone resin.

Comparative Use Example 1

An organic silicone resin was prepared according to the method of Use Example 1, except that 2,3-difluoro-4-methoxystyrene was replaced by styrene.

The modified organic silicone resin prepared in Use Examples 1 to 3 and the organic silicone resin prepared in Comparative Use Example 1 were separately used as a back coating solution to prepare a back coating of barcode thermal transfer ribbons, and a printing test was performed using a barcode thermal transfer ribbons printer. The specific criteria were as follows: (1) heat resistance: printing was performed at low, medium and high rates continuously for a specified time, based on no blurring in printing or cracking in the thermal transfer ribbons; a higher energy level and a higher rate means a better heat resistance, and vice versa; (2) adhesive force: the number of consecutive prints is used as an evaluation standard for adhesive force, specifically that until the print probe has gelatinous substances to affect printing; the more number of prints means a better adhesive force; (3) static friction coefficient and dynamic friction coefficient: the test was performed by GB/T 10006-1988 "Plastics—Film and Sheeting—Determination of the Coefficients of Friction"; a smaller value means a lower friction and a better lubricity; (4) noise evaluation: printed decibels were monitored in real time using a noise tester, forming a polyline change trend curve, and an average was calculated based on a stable noise; a smaller value means a smaller noise.

TABLE 1

Performance comparison data of barcode thermal transfer ribbons prepared based on modified organic silicone resins of Use Examples 1 to 3 and organic silicone resin of Comparative Use Example 1 for printing

| Test item | Test standard | Use Example 1 | Use Example 2 | Use Example 3 | Comparative Use Example 1 |
|---|---|---|---|---|---|
| Heat resistance | Heat resistance energy level | 30 | 29 | 30 | 28 |
| Adhesive force | Number of consecutive prints | 21000 | 20500 | 21000 | 19200 |
| | Gelatinous substance formation | None | None | None | None |

TABLE 1-continued

Performance comparison data of barcode thermal transfer ribbons prepared based on modified organic silicone resins of Use Examples 1 to 3 and organic silicone resin of Comparative Use Example 1 for printing

| Test item | | Test standard | Use Example 1 | Use Example 2 | Use Example 3 | Comparative Use Example 1 |
|---|---|---|---|---|---|---|
| Friction coefficient | Dynamic friction coefficient | GB/T 10006-1988 | 0.12 | 0.11 | 0.13 | 0.13 |
| | Static friction coefficient | | 0.21 | 0.19 | 0.18 | 0.18 |
| Printing noise | | Noise tester | 4 dB | 5 dB | 4 dB | 6 dB |

As can be seen from Table 1, the styrene derivative is introduced into the organic silicone resin to make the obtained modified organic silicone resin have a higher thermal stability; the modified organic silicone resin is used as a back coating solution for barcode thermal transfer ribbons to effectively improve a heat resistance. In addition, the styrene derivative is introduced into the organic silicone resin to effectively improve a smoothness of the obtained modified organic silicone resin; the modified organic silicone resin is used as a back coating solution for barcode thermal transfer ribbons to effectively reduce a printing noise. Meanwhile, the styrene derivative has a lower surface energy due to introduction of the fluorine atom; the styrene derivative is introduced into the organic silicone resin to effectively improve an adhesive force and bonding capacity of the obtained modified organic silicone resin.

The above description of examples is merely provided to help illustrate the method of the present disclosure and a core idea thereof. It should be noted that several improvements and modifications may be made by persons of ordinary skill in the art without departing from the principle of the present disclosure, and these improvements and modifications should also fall within the protection scope of the present disclosure. Various amendments to these embodiments are apparent to those of professional skill in the art, and the general principles defined herein may be implemented in other embodiments without departing from the spirit or scope of the present disclosure. Thus, the present disclosure is not limited to the examples shown herein but falls within the widest scope consistent with the principles and novel features disclosed herein.

What is claimed is:
1. A preparation method of a styrene derivative, comprising the following steps:
    mixing a methyltriphenylphosphonium bromide solution with a n-butyllithium (n-BuLi) solution in a protective atmosphere to obtain a phosphorus ylide reagent; and
    mixing the phosphorus ylide reagent with a 2,3-difluoro-4-methoxybenzaldehyde solution in a protective atmosphere to conduct a nucleophilic reaction, to obtain the styrene derivative having a structure shown in formula,

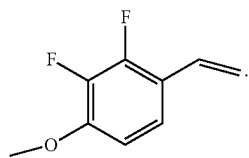

formula I

2. The preparation method according to claim 1, wherein the methyltriphenylphosphonium bromide solution has a concentration of 0.3 kg/L to 0.9 kg/L.
3. The preparation method according to claim 1, wherein the n-BuLi solution has a concentration of 2 mol/L to 3 mol/L.
4. The preparation method according to claim 1, wherein a mass of methyltriphenylphosphonium bromide in the methyltriphenylphosphonium bromide solution and a molar weight of n-BuLi in the n-BuLi solution have a ratio of (1-3) kg:(6-10) mol.
5. The preparation method according to claim 4, wherein the methyltriphenylphosphonium bromide solution has a concentration of 0.3 kg/L to 0.9 kg/L.
6. The preparation method according to claim 4, wherein the n-BuLi solution has a concentration of 2 mol/L to 3 mol/L.
7. The preparation method according to claim 1, wherein a method for mixing the methyltriphenylphosphonium bromide solution with the n-BuLi solution comprises the following step:
    adding the n-BuLi solution dropwise to the methyltriphenylphosphonium bromide solution under a protective atmosphere at −100° C. to 0° C.
8. The preparation method according to claim 1, wherein a method for mixing the phosphorus ylide reagent with the 2,3-difluoro-4-methoxybenzaldehyde solution comprises the following step:
    adding the 2,3-difluoro-4-methoxybenzaldehyde solution dropwise to the phosphorus ylide reagent under a protective atmosphere at −10° C. to 10° C.
9. The preparation method according to claim 1, wherein a solvent in the methyltriphenylphosphonium bromide solution and a solvent in the 2,3-difluoro-4-methoxybenzaldehyde solution each are an ethers-based organic solvent.
10. The preparation method according to claim 9, wherein the ethers-based organic solvent comprises one or more selected from the group consisting of tetrahydrofuran, methyltetrahydrofuran, diethyl ether, and methyl tert-butyl ether.
11. The preparation method according to claim 1, wherein a solvent in the n-BuLi solution is n-hexane.
12. The preparation method according to claim 1, wherein methyltriphenylphosphonium bromide in the methyltriphenylphosphonium bromide solution and 2,3-difluoro-4-methoxybenzaldehyde in the 2,3-difluoro-4-methoxybenzaldehyde solution have a mass ratio of (1-3):1.
13. The preparation method according to claim 1, wherein the 2,3-difluoro-4-methoxybenzaldehyde solution has a concentration of 0.3 kg/L to 1.5 kg/L.
14. The preparation method according to claim 1, wherein the nucleophilic reaction is conducted at 15° C. to 35° C. for 6 h to 12 h.
15. A modified organic silicone resin, prepared by the following raw materials: an acrylic acid derivative, a styrene derivative, methacryloxypropyl terminated polydimethylsiloxane, a free radical initiator, and an organic solvent, wherein the acrylic acid derivative, the styrene derivative, the methacryloxypropyl terminated polydimethylsiloxane, the free radical initiator, and the organic solvent have a mass ratio of (65-89):(1-5):(10-30):(0.1-2):(100-450); and the styrene derivative is the styrene derivative has a structure shown in formula I,

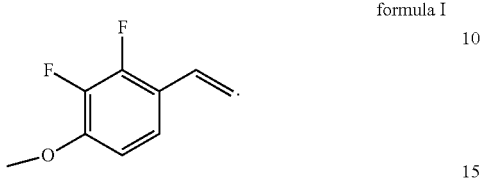

formula I

16. The modified organic silicone resin according to claim 15, wherein the acrylic acid derivative is one or more selected from the group consisting of methacrylic acid, acrylic acid, methacrylate, and acrylate.

17. The modified organic silicone resin according to claim 15, wherein the methacryloxypropyl terminated polydimethylsiloxane has a weight-average molecular weight of 10,000 to 40,000.

18. The modified organic silicone resin according to claim 15, wherein the free radical initiator comprises azobisisobutyronitrile and/or dibenzoyl peroxide.

19. The modified organic silicone resin according to claim 15, wherein the organic solvent comprises toluene and/or butanone.

* * * * *